United States Patent
Woo et al.

(10) Patent No.: US 7,514,921 B2
(45) Date of Patent: Apr. 7, 2009

(54) SYSTEM AND METHOD FOR VISUALIZING CONDUCTIVE AND CURRENT DENSITY DISTRIBUTION IN OBJECT

(75) Inventors: Eung Je Woo, Seongnam-si (KR); Jin Keun Seo, Seoul (KR); Oh In Kwon, Seoul (KR); Tae Seong Kim, Yongin (KR); Byung Il Lee, Yongin (KR); Suk Ho Lee, Seoul (KR)

(73) Assignee: University-Industry Cooperation Group of Kyunghee University, Yongin (KR)

( * ) Notice: Subject to any disclaimer, the term of this patent is extended or adjusted under 35 U.S.C. 154(b) by 80 days.

(21) Appl. No.: 10/595,980

(22) PCT Filed: Nov. 23, 2004

(86) PCT No.: PCT/KR2004/003026

§ 371 (c)(1),
(2), (4) Date: Aug. 31, 2006

(87) PCT Pub. No.: WO2005/051163

PCT Pub. Date: Jun. 9, 2005

(65) Prior Publication Data

US 2007/0088210 A1    Apr. 19, 2007

(30) Foreign Application Priority Data

Nov. 25, 2003  (KR)  .......... 10-2003-0083963
Jan. 12, 2004  (KR)  .......... 10-2004-0001993
Oct. 5, 2004   (KR)  .......... 10-2004-0079238

(51) Int. Cl.
*G01V 3/00* (2006.01)
*A61B 5/05* (2006.01)

(52) U.S. Cl. ............................... 324/300; 600/411
(58) Field of Classification Search ........... 324/300; 600/410, 411, 547
See application file for complete search history.

(56) References Cited

U.S. PATENT DOCUMENTS 6,397,095 B1 * 5/2002 Eyuboglu et al. .......... 600/411
2006/0224061 A1 * 10/2006 Woo et al. .................. 600/410

FOREIGN PATENT DOCUMENTS

WO   WO 2004/062464 A2   7/2004

* cited by examiner

Primary Examiner—Louis M Arana
(74) Attorney, Agent, or Firm—Workman Nydegger (57) ABSTRACT

System for visualizing conductivity and current density distributions including a plurality of current injecting devices (100) for injecting currents into a measuring object; a measuring unit (200) for measuring a magnetic flux density due to the currents injected into a measuring object; an operating unit (300) for selecting one pair of the current injecting devices in succession so as to inject currents of different directions into the measuring object, and calculating directional components of an anisotropic conductivity inside of the measuring object on the basis of the measured magnetic flux density; and displaying means for visualizing an inside of the measuring object by using the calculated directional components of the anisotropic conductivity.

33 Claims, 8 Drawing Sheets

SYSTEM AND METHOD FOR VISUALIZING CONDUCTIVE AND CURRENT DENSITY DISTRIBUTION IN OBJECT

TECHNICAL FIELD

The present invention relates to system and method for visualization of conductivity (or resistivity) and/or current density distributions of a measuring object, such as a human body, or a substance.

BACKGROUND ART

In general, X-ray, MRI, or ultrasound is used in visualization of an inside structure of the human body or the substance. However, the methods can not visualize electrical properties of the human body or the substance.

As an effort for solving the problem, a method for visualizing current density distribution of an inside of a measuring object using the MRI is initially suggested by a research team of the Toronto University in 1989, and, thereafter, there have been active researches related thereto. This is the Current Density Imaging (CDI) technique. In the present CDI, a magnetic flux density B due to an injected current I is measured by using MRI technique, and a current density J is calculated by using the Ampere's law $J=1/\mu_0 \nabla \times B$, for visualizing an inside current density distribution.

However, the CDI has a drawback in that rotation of the measuring object in an MRI scanner is required for obtaining the magnetic flux density B having three components Bx, By, and Bz. This is because the MRI scanner can only measure a z-directional component, a direction the same with a main magnetic field, of the flux density, i.e., Bz, when the measuring object is in the MRI scanner. That is, since the component the MRI scanner can measure at a time is only the Bz component, for obtaining all the required three components of the magnetic flux density vector, the present CDI technique has a serious drawback of requiring the measuring object (the human body, or the substance) to be rotated in the MRI scanner.

Meanwhile, as a known method for visualizing the electrical properties of the human body, or the substance, there has been Electrical Impedance Tomography (EIT) that has been under active research starting from late 1970s. The EIT provides an image of resistivity (or conductivity) distribution, an electrical property of the measuring object.

In the EIT mostly taking the human body as the measuring object, many electrodes are attached on a surface of the human body, for visualizing the resistivity distribution of an inside of the human body. The visualization of the human body 3according to the resistivity is made possible since tissues of the human body, such as blood, bones, lung, heart, and the like have electrical properties different from one another.

However, due to a fundamental drawback of the EIT, an image of the EIT is poor, to support only a low resolution. That is, EIT has a fundamental drawback in that a current-voltage data measured by EIT is extremely insensitive to variation of resistivity of an inside of the human body. Therefore, clinical application of EIT is not active, presently.

DISCLOSURE OF INVENTION

An object of the present invention, designed to solve the related art problem, is to provide system and method for visualization of conductivity and current density distribution, in which electrical properties (conductivity and current density) of a measuring object can be visualized in more accurate high resolution without rotating the measuring object.

Another object of the present invention is to provide system and method for visualization of conductivity and current density distribution, in which noises can be removed from magnetic flux density signals effectively and a high quality conductivity image can be produced.

The object of the present invention can be achieved by providing a system for visualizing conductivity and current density distributions including a plurality of current injecting devices for injecting currents into a measuring object, a measuring unit for measuring a magnetic flux density due to the currents injected into a measuring object, an operating unit for selecting one pair of the current injecting devices in succession so as to inject currents of different directions into the measuring object, and calculating directional components of an anisotropic conductivity inside of the measuring object on the basis of the measured magnetic flux density, and displaying means for visualizing an inside of the measuring object by using the calculated directional components of the anisotropic conductivity.

The selected pair of the current injecting devices apply the current to the measuring object, and one or more non-selected pairs of the current injecting devices measure a surface voltage of the measuring object.

The measuring unit measures the magnetic flux density corresponding to one direction parallel to a main magnetic field thereof.

The operating unit calculates an inside voltage and a surface voltage of the measuring object on the basis of an arbitrary conductivity, and calculates the directional components of the anisotropic conductivity on the basis of the calculated inside voltage and the measured magnetic flux density.

The operating unit calculates new directional components of the anisotropic conductivity on the basis of a calculated inside voltage depending on the calculated directional components, if an absolute value of a difference between the arbitrary conductivity and the calculated anisotropic conductivity is greater than a preset value.

The operating unit determines that the calculated anisotropic conductivity is a true conductivity, if an absolute value of the difference between the arbitrary conductivity and the calculated anisotropic conductivity is smaller than a present value.

The operating unit calculates a current density distribution inside of the measuring object on the basis of the calculated inside voltage and the measured magnetic flux density, and calculates a z-directional component on the basis of the calculated inside voltage and the calculated current density distribution.

The operating unit divides the measured magnetic flux density into a first part not including noises and a second part including the noises, removes the noises from the second part, and combines the first part and the second part.

In another aspect of the present invention, a method for visualizing conductivity and current density distributions includes (a) injecting currents of different directions into a measuring object through current injecting devices attached to a surface of the measuring object, (b) measuring a magnetic flux density due to the injected currents, (c) calculating directional components of an anisotropic conductivity inside of the measuring object on the basis of the measured magnetic flux density, and (d) visualizing an inside of the measuring object by using the calculated directional components of the anisotropic conductivity.

The injecting currents of different directions into the measuring object comprises selecting a pair of the current injecting devices in succession, injecting the currents into the measuring object in succession through the selected pair of the current injecting devices, and measuring a surface voltage of the measuring object through non-selected current injecting devices.

The measuring the magnetic flux density comprises measuring the magnetic flux density corresponding to one direction parallel to a main magnetic field.

The calculating the directional components of the anisotropic conductivity comprises calculating an inside voltage and a surface voltage of the measuring object on the basis of an arbitrary conductivity, and calculating the directional components of the anisotropic conductivity on the basis of the calculated inside voltage and the measured magnetic flux density.

The calculating the directional components of the anisotropic conductivity comprises multiplying or dividing the calculated directional components of the anisotropic conductivity by a ratio of the calculated surface voltage and a measured surface voltage of the measuring object.

The calculating the directional components of the anisotropic conductivity comprises calculating an absolute value of a difference of the arbitrary conductivity and the calculated anisotropic conductivity, and comparing the absolute value of the difference to a preset value. If the absolute value of the difference of the arbitrary conductivity and the measured anisotropic conductivity is greater than the preset value, new directional components of the anisotropic conductivity are calculated on the basis of a calculated inside voltage depending on the calculated directional components. If the absolute value of the difference of the arbitrary conductivity and the calculated anisotropic conductivity is smaller than a present value, it is determined that the calculated anisotropic conductivity is a true conductivity.

The calculating directional components of the anisotropic conductivity comprises calculating five directional components of the anisotropic conductivity on the basis of the calculated inside voltage and the measured magnetic flux density, calculating a current density distribution inside of the measuring object on the basis of the calculated inside voltage and the measured magnetic flux density, and calculating one directional component of the anisotropic conductivity on the basis of the calculated inside voltage and the calculated current density distribution.

In another aspect of the present invention, a system for visualizing conductivity and current density distributions includes a plurality of current injecting devices for injecting currents into a measuring object, a measuring unit for measuring a magnetic flux density due to the currents injected into a measuring object, and an operating unit for dividing the measured magnetic flux density into a first part not including noises and a second part including the noises, and combining the first part and the second part after removing the noises from the second part.

The operating unit removes the noises from the second part on the basis of an intensity variation of an MRI magnitude image, or removes the noises from the second part on the basis of a spatial gradient of an image corresponding to the second part.

The operating unit calculates a magnetic flux density of a portion in which the magnetic flux density is not measured, on the basis of the magnetic flux density measured at a border of the portion.

In another aspect of the present invention, a method for visualizing conductivity and current density distributions comprises (a) injecting currents into a measuring object through current injecting devices attached to a surface of the measuring object, (b) measuring a magnetic flux density of due to the injected currents, (c) dividing the measured magnetic flux density into a first part not including noises and a second part including the noises, (d) removing the noises from the second part, and (e) combining the first part and the second part.

The dividing the measured magnetic flux density into the first part and the second part comprises calculating the first part by applying the measured magnetic flux density to a preset algorithm, and calculating a difference between the measured magnetic flux density and the calculated first part.

The removing the noises from the second part comprises removing the noises from the second part on the basis of an intensity variation of an MRI magnitude image, or removing the noises from the second part on the basis of a spatial gradient of an image corresponding to the second part.

BRIEF DESCRIPTION OF DRAWINGS

The accompanying drawings, which are included to provide a further understanding of the invention, illustrate embodiment(s) of the invention and together with the description serve to explain the principle of the invention. In the drawings.

BEST MODE FOR CARRYING OUT THE INVENTION

Figure 1:
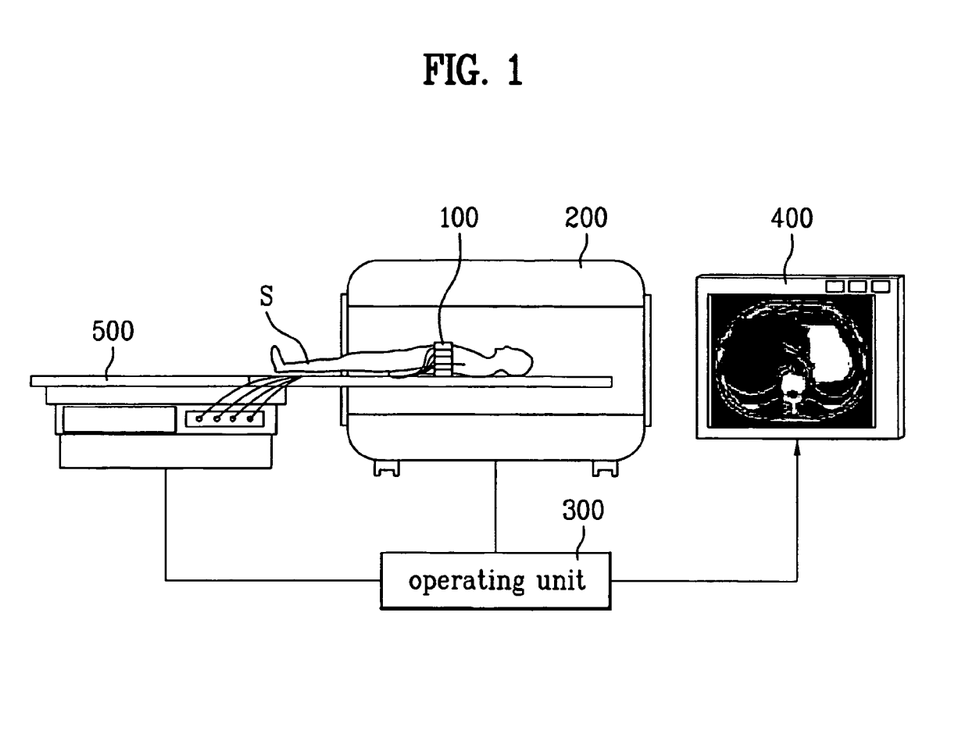
FIG. 1 illustrates a diagram of a system for visualizing conductivity and current density distribution in accordance with a preferred embodiment of the present invention.

Reference will now be made in detail to the preferred embodiments of the present invention, examples of which are illustrated in the accompanying drawings. In describing the embodiments, same parts will be given the same names and reference symbols, and repetitive description of which will be omitted. FIG. 1 illustrates a diagram of a system for visualizing conductivity and current density distribution in accordance with a preferred embodiment of the present invention.

Referring to FIG. 1, the system for visualizing conductivity and current density distributions includes current injecting devices 100 for injecting currents in directions different from one another into a measuring object, such as a human body or a substance, a magnetic flux density measuring unit (e.g., MRI scanner) 200 for measuring a magnetic flux density due to each of the currents, an operating unit 300 for calculating a conductivity (or resistivity) distribution and a current density distribution inside of the measuring object from the currents and the magnetic flux densities induced thereby, displaying means 400 for displaying the inside of the measuring object as an image of the conductivity and current density distributions, and a current source 500 for supplying the currents to the current injecting device 100.

Figure 2:
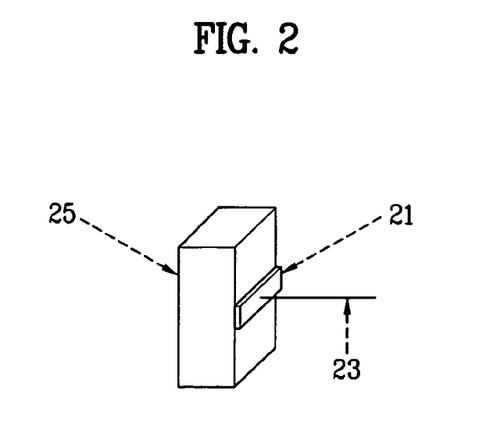
FIG. 2 illustrates a diagram showing a current injecting device in FIG. 1 in accordance with a first preferred embodiment of the present invention.

The current injecting device 100 includes an electrode 21 formed of a non-magnetic metal, such as copper, or a material having very high conductivity, and a wire for supplying the current to the electrode 21. Though direct attachment of the electrode 21 to a surface of the measuring object is possible, it is preferable that the electrode 21 is spaced apart from the surface of the measuring object for preventing distortion of the magnetic flux density at the surface of the measuring object. Therefore, as shown in FIG. 2, one embodiment of the current injecting device 100 of the present invention further includes an insulating container 25 having the electrode 21 attached thereto for putting the electrode 21 on a place spaced apart from the measuring object. The insulating container 25 has one surface having the electrode 21 attached thereto, and the other surface to be brought into contact with the measuring object in an opened state. The insulating container 25 is stuffed with sponge having an electrolyte gel or electrolyte solution absorbed therein. The sponge having an electrolyte gel or electrolyte solution absorbed therein makes uniform flow of the current from the electrode 21 in the insulating container 25. Thus, by putting the electrode on a place spaced apart from the surface of the measuring object by using the insulating container 25, and supplying the current to the measuring object uniformly by using the sponge having the electrolyte gel or electrolyte solution absorbed therein, distortion of an MRI image at the surface of the measuring object in contact with the electrode 21 can be reduced.

Figure 3A:
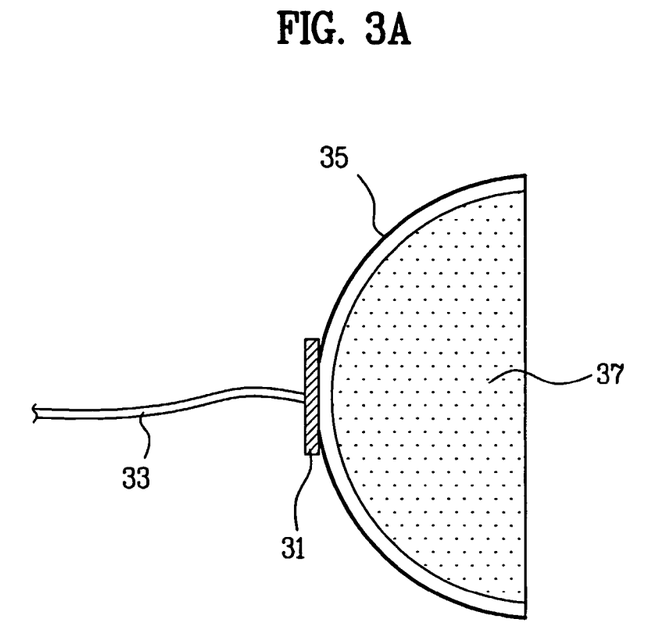
FIGS. 3A and 3B illustrate diagrams each showing another embodiment of the current injecting device in FIG. 1.
Figure 3B:
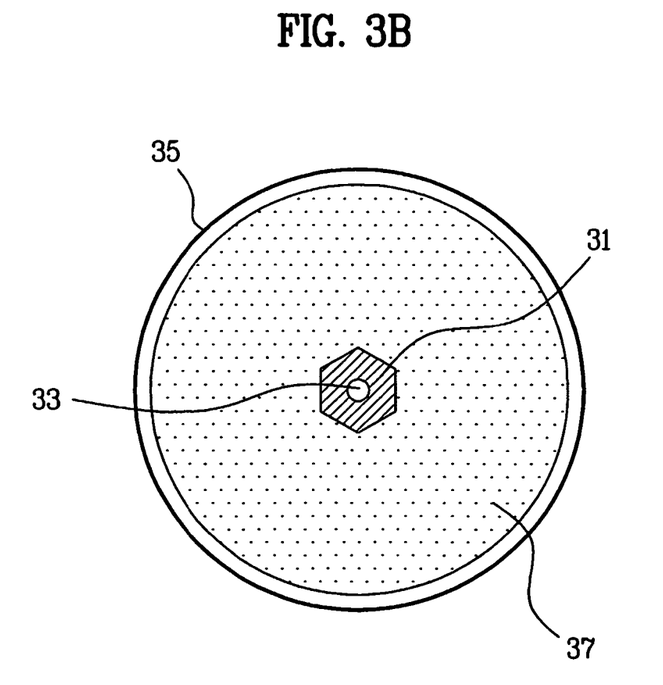

Referring to FIGS. 3A and 3B, another embodiment of the current injecting device 100 of the present invention includes an electrode 31, a wire 33 connected to the electrode 31, an semispherical insulating container 35 having the electrode 31 attached thereto. The insulating container 35 has one side having the electrode 31 attached thereto, and the other surface to be brought into contact with the measuring object 'S' in an opened state. The insulating container 35 is stuffed with sponge 37 having the electrolyte gel or electrolyte solution absorbed therein. The sponge 37 may be replaced by only the electrolyte gel.

Figure 4:
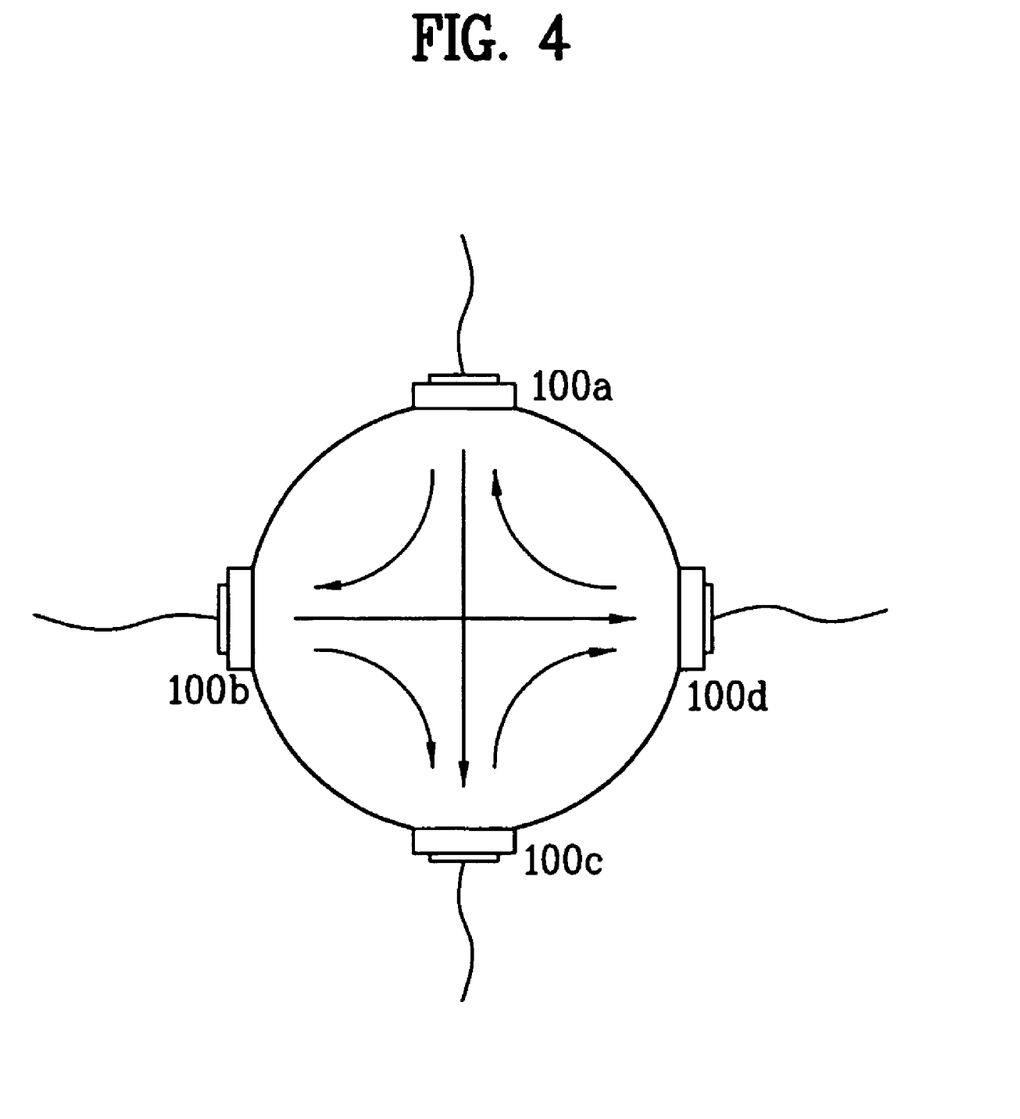
FIGS. 4 illustrates a diagram showing each showing current flows in the measuring object and each flow corresponds to one of six different injection currents.

Referring to FIG. 4, the current injecting devices 100 are attached to a circumference of the measuring object 'S', and the current is made to flow only to one pair of the current injecting devices 100 at a time, such that the current flows through the inside of the measuring object 'S' with the one pair of the current injecting devices 100. If it is assumed that a number of the current injecting devices 100 is 'E', a number 'N' of cases of the pairs of the current injecting devices 100 for injecting the current into the measuring object 'S' is E(E−1)/2. This is equal to a number of current paths in the measuring object 'S'. A current between the pair of current injecting devices 100 is represented with $I^j$ (j=1, 2, - - - , N). The current $I^j$ induces a current density $J^j$ ($J^j x$, $J^j y$, $J^j z$) in the measuring object 'S'.

The MRI scanner 200 measures a magnetic flux density $B^j$ in the measuring object 'S' due to the current $I^j$, particularly, a z-directional magnetic flux density $B^j z$ parallel to a main magnetic field of the MRI scanner 200. That is, the MRI scanner 200 measures magnetic flux densities $B^1 z$, $B^2 z$, $B^3 z$, - - - , $B^N z$ due to currents $I^1$, $I^2$, $I^3$, - - - , $I^N$ injected into the measuring object 'S', respectively.

The operating unit 300 selects one of the pairs of the current injecting devices 100 in succession, and controls the one of the pair of the current injecting devices to inject the current into the measuring object 'S'. The operating unit 300 also applies the magnetic flux density $B^j z$ measured by the MRI scanner 200 to a preset algorithm, and calculates a conductivity σ and a current density $J^j$ inside of the measuring object 'S'. Since the conductivity σ is an inversion of the resistivity ρ, the conductivity σ can be represented with 1/ρ. Then, the displaying means 400 visualizes the inside of the measuring object 'S' according to the conductivity σ and the current density $J^j$.

Optionally, the operating unit 300 may remove the noises from the measured magnetic flux density $B^j z$. The operating unit 300 divides the measured magnetic flux density $B^j z$ into a first magnetic flux density part not including the noises and a second magnetic flux density part including the noises, and synthesizes the first magnetic flux density part and the second magnetic flux density part after removing the noises from the second magnetic flux density part.

A method for visualizing conductivity and current density distributions in accordance with a preferred embodiment of the present invention, and an algorithm applied thereto will be described, in detail.

FIRST EMBODIMENT

The current injecting devices 100 are attached to a circumference of a measuring object 'S', i.e., a human body, and injects the currents in six directions into the measuring object 'S' in order to induce a three-dimensional anisotropic conductivity. The currents to be injected in six directions are generated by at least the four current injecting devices. A matrix of the anisotropic conductivity A is as follows.

$$A = \begin{bmatrix} \sigma_{xx} & \sigma_{xy} & \sigma_{xz} \\ \sigma_{yx} & \sigma_{yy} & \sigma_{yz} \\ \sigma_{zx} & \sigma_{zy} & \sigma_{zz} \end{bmatrix} = \begin{bmatrix} \sigma_{11} & \sigma_{12} & \sigma_{13} \\ \sigma_{21} & \sigma_{22} & \sigma_{23} \\ \sigma_{31} & \sigma_{32} & \sigma_{33} \end{bmatrix}$$

The anisotropic conductivity 'A' has nine directional components. The anisotropic conductivity 'A' practically includes the six directional components because the component $\sigma_{12}$ is identical with the component $\sigma_{21}$, the component $\sigma_{13}$ is identical with the component $\sigma_{31}$, and the component $\sigma_{23}$ is identical with the component $\sigma_{32}$. Therefore, the current injecting devices 100 inject the currents in at least the six directions into the measuring object 'S' in order to induce the anisotropic conductivity including the six components. A method for visualizing conductivity and current density distributions in accordance with an example in which the currents are injected into the measuring object 'S' in seven directions, will be described.

Figure 5:
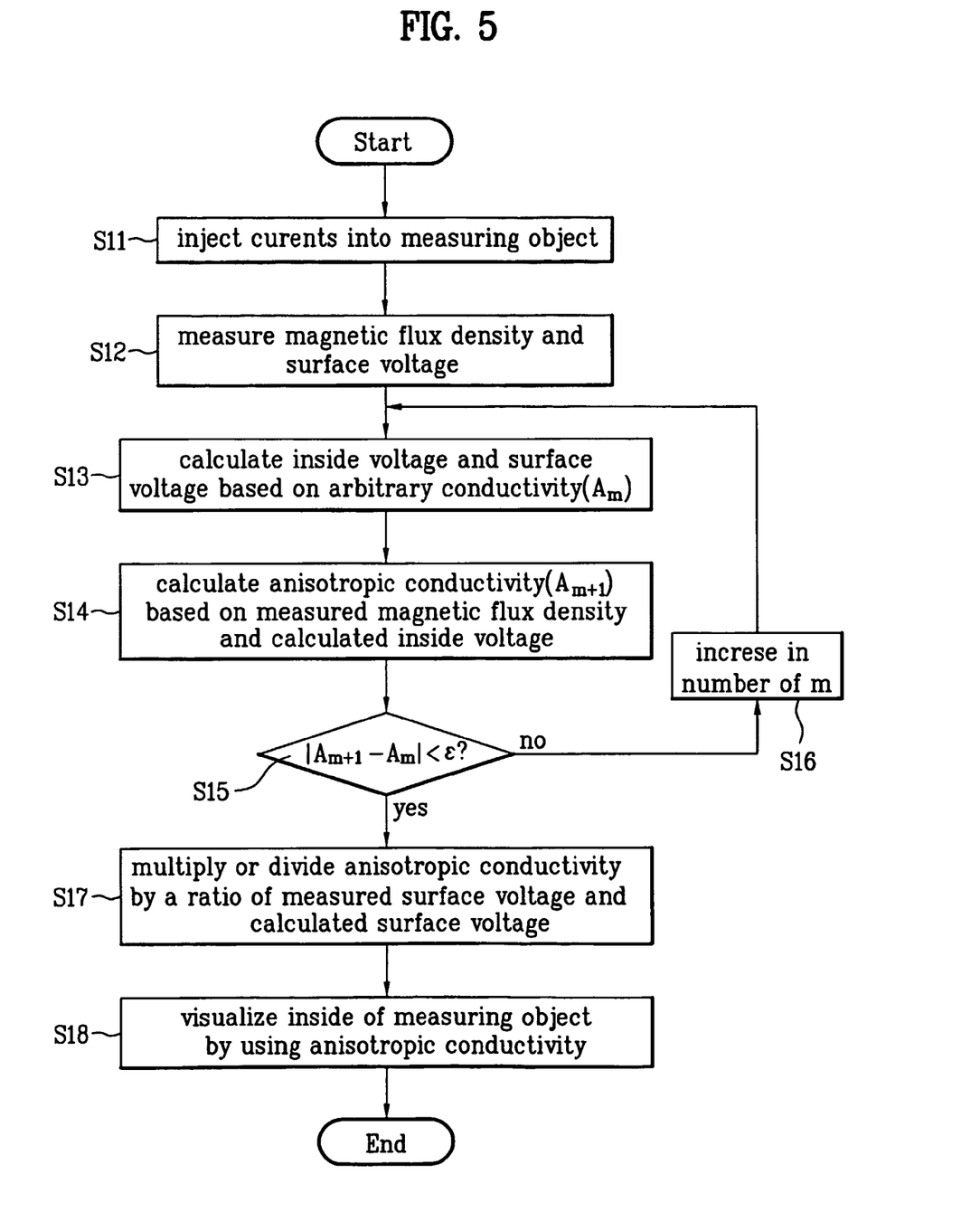
FIG. 5 illustrates a flow chart showing a method for visualization of conductivity and current density distribution in accordance with the present invention.

The measuring object 'S' is placed in an MRI scanner 200, and the pairs of the current injecting devices 100 are selected one by one in succession, and the current $I^j$ (j=1, 2, - - - , 7) is supplied to an inside of the measuring object 'S' through the pair of the current injecting devices 100 selected in succession (S11). For an example, as shown in FIG. 4, in a case in which four current injecting devices 100a, 100b, 100c, and 100d are attached to a circumference of the measuring object 'S', the currents are supplied to the inside of the measuring object 'S' in six directions in succession. In these instances, the MRI scanner 200 measures the magnetic flux densities $B^1 z$, $B^2 z$, . . . $B^7 z$ due to the currents $I^1$, $I^2$, . . . $I^7$ injected into the measuring object 'S' respectively. The MRI scanner 200 measures 'z' direction components of the magnetic flux densities, only. Also, the non-selected current injecting devices 100 measure a surface voltage $V^j|_{\partial S}$ of the measuring object 'S' (S12).

Then, the operating unit 300 applies the magnetic flux densities $B^1z\ B^2z, \ldots B^7z$ measured by the MRI scanner 200 and the surface voltage $V^j|_{\partial S}$ measured by the non-selected current injecting devices to a preset algorithm, and calculates the anisotropic conductivity 'A' and the current density $J^j$ inside of the measuring object 'S'.

Equations to be used for the algorithm in the first embodiment will be described, where, S: a measuring object, $\partial S$: a surface of the measuring object, $g^j$: a component of a current density of an injected current at a surface of the measuring object, n: a unit normal vector at the surface of the measuring object, $V^j$: a voltage of the injected current in the measuring object.

The magnetic flux densities $B^1z, B^2z, \ldots B^7z$ can be expressed as the following equation (1) based on the Ampere's law $$-\frac{1}{\mu_0}\nabla^2 B = \nabla \times J$$

and the Ohm's law $J=-A\nabla V$. The symbol $\mu_0$ is a magnetic permeability in a free space.

$$\frac{1}{\mu_0}\begin{bmatrix}\nabla^2 B_z^1 \\ \vdots \\ \nabla^2 B_z^7\end{bmatrix} = \begin{bmatrix}\partial_x V^1 & \partial_y V^1 & \partial_z V^1 & \partial_x^2 V^1 - \partial_y^2 V^1 & \partial_x \partial_y V^1 & \partial_x \partial_z V^1 & -\partial_y \partial_z V^1 \\ \vdots & \vdots & \vdots & \vdots & \vdots & \vdots & \vdots \\ \partial_x V^7 & \partial_y V^7 & \partial_z V^7 & \partial_x^2 V^7 - \partial_y^2 V^7 & \partial_x \partial_y V^7 & \partial_x \partial_z V^7 & -\partial_y \partial_z V^7\end{bmatrix}\begin{bmatrix}-\partial_y \sigma_{11} + \partial_x \sigma_{12} \\ -\partial_y \sigma_{12} + \partial_x \sigma_{22} \\ -\partial_y \sigma_{13} + \partial_x \sigma_{23} \\ \sigma_{12} \\ -\sigma_{11} + \sigma_{22} \\ \sigma_{23} \\ \sigma_{13}\end{bmatrix} \quad (1)$$

If the measured magnetic flux density $B^jz$ and the voltage $V^j$ are substituted into the equation (1), the components of the anisotropic conductivity 'A' may be obtained. However, it is impossible to obtain the actual components of the anisotropic conductivity 'A' because the voltage $V^j$ inside the measuring object 'S' cannot be measured. In order to obtain the voltage $V^j$, an iterative algorithm is used. If the voltage values are obtained by using the iterative algorithm, the components $\sigma_{11}, \sigma_{12}, \sigma_{13}, \sigma_{22}, \sigma_{23}$ of the anisotropic conductivity 'A' except the component $\sigma_{33}$ may be calculated by substituting the voltage values into the equation (1).

The component $\sigma_{33}$ may be calculated by substituting the calculated components $\sigma_{11}, \sigma_{12}, \sigma_{13}, \sigma_{22}, \sigma_{23}$, the voltage $V^j$, and the current densities $J^jx, J^jy$ into the following equation (2).

$$\begin{pmatrix}\partial_z V^1 & \partial_z^2 V^1 \\ \vdots & \vdots \\ \partial_z V^7 & \partial_z^2 V^7\end{pmatrix}\begin{pmatrix}\sigma_{33} \\ \partial_z \sigma_{33}\end{pmatrix} = \quad (2)$$

-continued $$\begin{pmatrix}-\partial_x J_x^1 - \partial_y J_y^1 - \partial_z (\sigma_{13}\partial_x V^1 + \sigma_{23}\partial_y V^1) \\ \vdots \\ -\partial_x J_x^7 - \partial_y J_y^7 - \partial_z (\sigma_{13}\partial_x V^7 + \sigma_{23}\partial_y V^7)\end{pmatrix}$$

Wherein, the current densities $J^jx, J^jy$ are may obtained from the following equations.

$$(J_x^j, J_y^j, J_z^j) = -A\nabla V^j = -\begin{bmatrix}\sigma_{11} & \sigma_{12} & \sigma_{13} \\ \sigma_{21} & \sigma_{22} & \sigma_{23} \\ \sigma_{31} & \sigma_{32} & \sigma_{33}\end{bmatrix}\begin{bmatrix}\partial_x V^j \\ \partial_y V^j \\ \partial_z V^j\end{bmatrix}$$

$$-\frac{1}{\mu_0}\nabla^2 B_z^j = \nabla \times \begin{bmatrix}J_x^j \\ J_y^j\end{bmatrix}$$

The value of the voltage $V^j$ should be obtained in order to calculate the components of the anisotropic conductivity by using the equations (1), (2). The value of the voltage may be obtained by using an iterative algorithm and the following equation (3).

$$\nabla \cdot (A\nabla V^j) = 0 \quad (j = 1, 2, \ldots 7) \quad (3)$$

-continued $$-A\nabla V^j \cdot n = g^j$$

The equation (3) is to calculate the voltage $V^j$ inside the measuring object 'S'.

The component $g^j$ of the current density is zero (0) at the surface of the measuring object 'S' not in contact with the selected pair of the current injecting devices 100. If the anisotropic conductivity 'A', the injected current $I^j$, and positions of the current injecting devices 100 are known, the voltage $V^j$ can be calculated by a calculating method, such as FEM (Finite Element Method).

The anisotropic conductivity 'A' should be known in order to calculate the voltage $V^j$ by using the equation (3), The voltage $V^j$ should be known in order to calculate the anisotropic conductivity 'A' by using the equations (1), (2). A process for calculating the conductivity 'A' and the voltage $V^j$ at the operating unit 300 by using the foregoing equations (1), (2), (3) will be described below in detail.

The initial conductivity $A_m$ (m=0) is set, and the initial conductivity $A_m$ (m=0) and the current density component $g^j$ at the surface of the measuring object 'S' are substituted into the following equation (4), to calculate voltages $V^j_{m+1}$ and $V^j_{m+1}|_{\partial S}$ at the inside and the surface of the measuring object 'S' (S13). The initial conductivity Am (m=0) may be a constant value if it is assumed that the initial conductivity Am is isotropic, or may has the directional components acknowledged according to the tissues of the body. The inner voltage $V^j_{m+1}$ and the surface voltage $V^j_{m+1}|_{\partial S}$ are calculated based on the initial conductivity Am. The current density component $g^j$ can be known from the current $I^j$ (j=1, 2, - - -, 7).

$$\nabla \cdot (A_m \nabla V^j_{m+1}) = 0 \ (j = 1, 2, \ldots 7) \quad (4)$$
$$-A_m \nabla V^j_{m+1}|_{\partial S} \cdot n = g^j$$

After the inner voltage $V^j_{m+1}$ corresponding to the initial conductivity is obtained, the inner voltage $V^j_{m+1}$ and the measured magnetic flux density $B^j_z$ are substituted into the equation (1) and the equation (2) in order to calculate the components of the anisotropic conductivity $A_{m+1}$ (S14). The calculated anisotropic conductivity $A_{m+1}$ is closer to a true conductivity than the conductivity $A_m$, because the calculated conductivity $A_{m+1}$ has taken an true magnetic flux density $B^j_z$ inside of the measuring object 'S' into account.

Moreover, in the present invention, for obtaining the conductivity close to the true value, an iterative form of algorithm is used. That is, alike the following equation $\|\sigma_{m+1} - \sigma_m\| < \epsilon$, a difference between a conductivity $A_m$ in a prior step and a conductivity $A_{m+1}$ in the present step is calculated, and it is determined whether an absolute value of the difference is smaller than a preset value '$\epsilon$' or not (S15). The equations (1), (2), and (4) are calculated repeatedly by increasing the 'm' until the calculated difference becomes smaller than the preset value '$\epsilon$' (S16). If the absolute value of the difference of the conductivity $A_m$ in the prior step and the conductivity $A_{m+1}$ in the present step is smaller than the preset value '$\epsilon$', the conductivity $A_{m+1}$ is taken as the true conductivity. Then the measuring object 'S' is visualized by using the calculated conductivity $A_{m+1}$ (S18).

However, even if the calculated conductivity $A_{m+1}$ has taken the true magnetic flux density $B^j_z$ into account, the calculated conductivity $A_{m+1}$ may differ from the true conductivity. That is, though the calculated conductivity $A_{m+1}$ has a value varied with the magnetic flux density $B^j_z$, the calculated conductivity $A_{m+1}$ may be greater or smaller than the true conductivity by a multiplication of a constant. For eliminating the difference between the calculated conductivity $A_{m+1}$ and the true conductivity, in the present invention, the measured surface voltage $V^j|_{\partial S}$ and the calculated surface voltage $V_{m+1}{}^j|_{\partial S}$ may be used for scaling the conductivity $A_{m+1}$. In other words, according to a ratio of the measured surface voltage $V^j|_{\partial S}$ to the calculated surface voltage $V_{m+1}{}^j|_{\partial S}$, the conductivity $A_{m+1}$ is multiplied or divided by a constant value. Thus, the conductivity $A_{m+1}$ is calculated correctly.

In addition, the conductivity $A_{m+1}$ is substituted into the equation (4) to calculated a voltage depending on the conductivity $A_{m+1}$, i.e., the voltage $V^j$ inside of the measuring object 'S' is calculated. Then, by using the conductivity $A_{m+1}$ and the voltage $V^j$, the current density $J^j$ is calculated, and by using the current density $J^j$, the inside of the measuring object 'S' is visualized.

SECOND EMBODIMENT

The current is injected into the measuring object 'S' in two directions or more in succession in order to induce a conductivity $\sigma$, and is generated by at least 3 current injecting devices 100.

The measuring object 'S' is placed in the MRI scanner 200, and the pairs of the current injecting devices 100 are selected one by one in succession, and the current $I^j$ (j=1, 2, - - -, N) is supplied to an inside of the measuring object 'S' through the pair of the current injecting devices 100 selected in succession. The MRI scanner 200 measures the magnetic flux densities $B^1z, B^2z, \ldots B^Nz$ due to the currents $I^1, I^2, \ldots I^N$ injected into the measuring object 'S' respectively, the non-selected current injecting devices 100 measure a surface voltage $V^j|_{\partial S}$ of the measuring object 'S' when the selected pair of the current injecting devices 100 injects the current into the measuring object 'S'.

Then, the operating unit 300 applies the magnetic flux densities $B^1z\ B^2z, \ldots B^Nz$ measured by the MRI scanner 200 and the surface voltage $V^j|_{\partial S}$ measured by the non-selected current injecting devices to a preset algorithm, and calculates the conductivity $\sigma$ and the current density $J^j$ inside of the measuring object 'S'.

The conductivity $\sigma$ is calculated on the basis of the Maxwell equation $\nabla \times B^j = \mu_0 J^j$ including a magnetic flux density and a current density. The Maxwell equation is multiplied by a vector function $\Psi$, and is integrated three times, then the following equation (5) depending on the Ohm's law $J^j = -\sigma \nabla V^j$ may be obtained.

$$\int_S \nabla \times B^j \cdot \vec{\Psi} dr = -\mu_0 \int_S \sigma \nabla V^j \cdot \vec{\Psi} dr \quad (5)$$

Wherein, $\vec{r} = (x,y,z)$. Since the only component $B^jz$ can be measured without rotating the measuring object 'S', the components $B^jx$ and $B^jy$ of the magnetic flux density should be removed from the equation (5). Thus, the function group, such as the following equation (6), is determined.

$$T := \left( \psi \in H^1(S) \text{:for all } \vec{r} \in \partial S, \ \begin{array}{ll} \frac{\partial \psi}{\partial x}(\vec{r}) = 0 = \frac{\partial \psi}{\partial x}(\vec{r}) & \text{if } n \cdot \vec{e_3} = 0 \\ \frac{\partial \psi}{\partial z}(\vec{r}) = 0 & \text{if } n \times \vec{e_3} = 0 \end{array} \right) \quad (6)$$

Wherein, $\vec{e}_3 = (0,0,1)$. $H^1(S)$ is a square integrable function. The divergence theorem induces the following equation (7) by substituting the function $$\Psi = \left( \frac{\partial \psi}{\partial y}, -\frac{\partial \psi}{\partial x}, 0 \right)$$

into the equation (5).

$$\int_S \sigma L \tilde{\nabla} V^j \cdot \tilde{\nabla} \psi \, dr = \frac{1}{\mu_0} \int_S \nabla B^j_z \cdot \nabla \psi \, dr \quad (7)$$

Wherein, the symbol $\nabla$ is $$\left(\frac{\partial}{\partial x}, \frac{\partial}{\partial y}\right)$$

and the symbol $$L \text{ is } \begin{bmatrix} 0 & 1 \\ -1 & 0 \end{bmatrix}.$$

If the measured magnetic flux density $B^j z$ and the voltage $V^j$ are substituted into the equation (7), the conductivity $\sigma$ may be obtained. However, it is impossible to obtain the actual conductivity because the voltage $V^j$ inside the measuring object 'S' cannot be measured. In order to obtain the voltage $V^j$, an iterative algorithm based on the following equation (8) is used.

$$\int_S \sigma_{m+1} L \tilde{\nabla} V_m^j \cdot \tilde{\nabla} \psi \, dr = \frac{1}{\mu_0} \int_S \nabla B_z^j \cdot \nabla \psi \, dr \qquad (8)$$

Wherein, the conductivity $\sigma_{m+1}$ is the newly calculated conductivity and the voltage $V^j_m$ is the calculated voltage depending on the previous conductivity $\sigma_m$. The voltage $V^j_m$ may be calculated by the following equation (9) and a calculating method, such as FEM (Finite Element Method).

$$\nabla \cdot (\sigma_m \nabla V^j_m) = 0, \text{ inside } S$$

$$-\sigma_m \nabla V^j_m \cdot n = g^j, \text{ on } \partial S$$

$$\int_{\partial S} V^j_m = 0 \qquad (9)$$

The component $g^j$ of the current density is zero (0) at the surface of the measuring object 'S' not in contact with the selected pair of the current injecting devices 100.

A process for calculating the conductivity $\sigma_{m+1}$ and the voltage $V^j_m$ at the operating unit 300 by using the foregoing equations (8) and (9) will be described below in detail.

The initial conductivity $\sigma_m$ (m=0) is set, and the initial conductivity $\sigma_m$ and the current density component $g^j$ at the surface of the measuring object 'S' are substituted into the following equation (9), to calculate voltages $V^j_m$ and $V^j_m|_{\partial S}$ at the inside and the surface of the measuring object 'S'. The initial conductivity $\sigma_m$ may be a constant value if it is assumed that the initial conductivity $\sigma_m$ is isotropic, or may has the directional components acknowledged according to the tissues of the body. The inner voltage $V^j_m$ and the surface voltage $V^j_m|_{\partial S}$ are calculated based on the initial conductivity $\sigma_m$. The current density component $g^j$ can be known from the current $I^j$ (j=1, 2, - - - , N).

After the inner voltage $V^j_m$ corresponding to the initial conductivity $\sigma_m$ is obtained, the inner voltage $V^j_m$ and the measured magnetic flux density $B^j_z$ are substituted into the equation (8) in order to calculate the conductivity $\sigma_{m+1}$. The calculated $\sigma_{m+1}$ is closer to a true conductivity than the conductivity $\sigma_m$, because the calculated conductivity $\sigma_{m+1}$ has taken an true magnetic flux density $B^j_z$ inside of the measuring object 'S' into account.

Moreover, in the present invention, for obtaining the conductivity close to the true value, an iterative form of algorithm is used. That is, alike the following equation $\iiint_S |\sigma_{m+1}(\vec{r}) - \sigma_m(\vec{r})|^2 d\vec{r}$, a difference between the conductivity $\sigma_m$ in a prior step and the conductivity $\sigma_{m+1}$ calculated in the present step is calculated, and it is determined whether an absolute value of the difference is smaller than a preset value '$\epsilon$' or not. The equations (8) and (9) are calculated repeatedly by increasing the 'm' until the calculated difference becomes smaller than the preset value '$\epsilon$'. If the absolute value of the difference of the conductivity $\sigma_m$ in the prior step and the conductivity $\sigma_{m+1}$ in the present step is smaller than the preset value '$\epsilon$', the conductivity $\sigma_{m+1}$ is taken as the true conductivity. Then the measuring object 'S' is visualized by using the calculated conductivity $\sigma_{m+1}$.

However, even if the calculated conductivity $\sigma_{m+1}$ has taken the true magnetic flux density $B^j_z$ into account, the calculated conductivity $\sigma_{m+1}$ may differ from the true conductivity. For example, though the calculated conductivity $\sigma_{m+1}$ has a value varied with the magnetic flux density $B^j_z$, the calculated conductivity $\sigma_{m+1}$ may be greater or smaller than the true conductivity. For eliminating the difference between the calculated conductivity $\sigma_{m+1}$ and the true conductivity, in the present invention, the measured surface voltage $V^j|_{\partial S}$ and the calculated surface voltage $V_{m+1}{}^j|_{\partial S}$ may be used for scaling the conductivity $\sigma_{m+1}$. In other words, the conductivity $\sigma_{m+1}$ is multiplied or divided by a ratio of the measured surface voltage $V^j|_{\partial S}$ to the calculated surface voltage $V_{m+1}{}^j|_{\partial S}$. Thus, the conductivity $\sigma_{m+1}$ is calculated correctly.

In addition, the conductivity $\sigma_{m+1}$ is substituted into the equation (9) to calculated a voltage depending on the conductivity $\sigma_{m+1}$, i.e., the voltage $V^j$ inside of the measuring object 'S' is calculated. Then, by using the conductivity $\sigma_{m+1}$ and the voltage $V^j$, the current density $J^j$ is calculated, and by using the current density $J^j$, the inside of the measuring object 'S' is visualized.

A process for calculating the conductivity based on first partial derivatives of the measured magnetic flux density $B^j_z$ using another equations will be described below in detail.

The vector $(-J^j_y, J^j_x, 0)$ can be expressed as the following equation (10).

$$(-J^j_y, J^j_x, 0) = \nabla w^j + \nabla \times W^j \qquad (10)$$

Wherein, the symbol $w^j$ is a scalar function and the symbol $W^j$ is a vector function $$W^j(\vec{r}) = \int\int_{\partial S} \frac{1}{4\pi |\vec{r} - \vec{r'}|} \frac{\partial}{\partial z}\left[\sigma \nabla V^j(\vec{r'})\right] dA.$$

The symbol dA is referred to a square measure.

The following equation (11) representing the relation between the flux density $B^j_z$ and the scalar function $w^j$ may be obtained by using the Maxwell equation $1/\mu_0 \nabla \times B^j = J^j$ including the magnetic flux density $B^j = (B^j_x, B^j_y, B^j_z)$ and the current density $J^j = (J^j_x, J^j_y, J^j_z)$.

$$\frac{1}{\mu_0} B_z^j = w^j + h^j + v^j \qquad (11)$$

$$\begin{cases} \nabla^2 h^j = 0 & \text{in } S \\ T \cdot \nabla h^j = (n_x, n_y, 0) \cdot J^j - \frac{1}{\mu_0} T \cdot \nabla B_z^j & \text{on } \partial S \end{cases}$$

-continued $$\begin{cases} \nabla^2 v^j = 0 & \text{in } S \\ \nabla v^j \cdot T = \nabla \times W \cdot T & \text{on } \partial S \end{cases}$$

Wherein, the symbol T is a tangent vector $T=(-n_y, n_x, 0)$ corresponding to $\partial S$.

The following equation (12) may be obtained by substituting the equation (11) into the equation (10).

$$J_x^j = \frac{\partial H^j}{\partial y} + L[V^j], \quad J_y^j = -\frac{\partial H^j}{\partial y} - M[V^j] \quad (12)$$

Wherein, the symbol $H^j$ represents $$h^j + \frac{1}{\mu_0} B_z^j,$$

the function $L[V^j]$: represents $$\frac{\partial v^j}{\partial y} - \frac{\partial W_z^j}{\partial x} + \frac{\partial W_x^j}{\partial z},$$

and the function $M[V^j]$: represents $$\frac{\partial v^j}{\partial x} + \frac{\partial W_z^j}{\partial y} - \frac{\partial W_y^j}{\partial z}.$$

The functions $L[V^j]$: and $M[V^j]$: are determined on the basis of the measured data $V^j$, $g^j$, and $B_z^j$.

The following equation (13) may be obtained by using the equation (12) and the Ohm's law.

$$\sigma = \frac{\left| -\frac{\partial V^j}{\partial x}\left(\frac{\partial H^j}{\partial y} + L[V^j]\right) + \frac{\partial V^j}{\partial y}\left(\frac{\partial H^j}{\partial x} + M[V^j]\right) \right|}{\left(\frac{\partial V^j}{\partial x}\right)^2 + \left(\frac{\partial V^j}{\partial y}\right)^2} \quad (13)$$

If the measured magnetic flux density $B^j z$ and the voltage $V^j$ are substituted into the equation (13), the conductivity $\sigma$ may be obtained. However, it is impossible to obtain the actual conductivity because the voltage $V^j$ inside the measuring object 'S' cannot be measured. In order to obtain the voltage $V^j$, an iterative algorithm based on the following equation (14) is used.

$$\sigma_{m+1} = \frac{\left| -\frac{\partial V_m^j}{\partial x}\left(\frac{\partial H^j}{\partial y} + L[V_m^j]\right) + \frac{\partial V_m^j}{\partial y}\left(\frac{\partial H^j}{\partial x} + M[V_m^j]\right) \right|}{\left(\frac{\partial V_m^j}{\partial x}\right)^2 + \left(\frac{\partial V_m^j}{\partial y}\right)^2} \quad (14)$$

Wherein, the conductivity $\sigma_{m+1}$ is the newly calculated conductivity and the voltage $V_m^j$ is the calculated voltage depending on the previous conductivity $\sigma_m$. The voltage $V_m^j$ may be calculated by using a calculating method depending on the following equation (15), such as FEM (Finite Element Method).

$$\nabla \cdot (\sigma_m \nabla V_m^j) = 0 \text{ inside } S$$

$$-\sigma_m \nabla V_m^j \cdot \nu = g^j \text{ on } \partial S$$

$$\int_{\partial S} V_m^j = 0 \quad (15)$$

The component $g^j$ of the current density is zero (0) at the surface of the measuring object 'S' not in contact with the selected pair of the current injecting devices 100.

A process for calculating the conductivity $\sigma_{m+1}$ and the voltage $V_m^j$ at the operating unit 300 by using the foregoing equations (14) and (15) will be described below in detail.

The initial conductivity $\sigma_m$ (m=0) is set, and the initial conductivity $\sigma_m$ and the current density component $g^j$ at the surface of the measuring object 'S' are substituted into the following equation (15), to calculate voltages $V_m^j$ and $V_m^j|_{\partial S}$ at the inside and the surface of the measuring object 'S'. The initial conductivity $\sigma_m$ may be a constant value if it is assumed that the initial conductivity $\sigma_m$ is isotropic, or may has the directional components acknowledged according to the tissues of the body. The inner voltage $V_m^j$ and the surface voltage $V_m^j|_{\partial S}$ are calculated based on the initial conductivity $\sigma_m$.

After the inner voltage $V_m^j$ corresponding to the initial conductivity $\sigma_m$ is obtained, the inner voltage $V_m^j$ and the measured magnetic flux density $B_z^j$ are substituted into the equation (14) in order to calculate the conductivity $\sigma_{m+1}$. The calculated $\sigma_{m+1}$ is closer to a true conductivity than the conductivity $\sigma_m$, because the calculated conductivity $\sigma_{m+1}$ has taken an true magnetic flux density $B_z^j$ inside of the measuring object 'S' into account.

Moreover, in the present invention, for obtaining the conductivity close to the true value, an iterative form of algorithm is used. That is, alike the following equation $\iiint_S |\sigma_{m+1}(\vec{r}) - \sigma_m(\vec{r})|^2 d\vec{r}$, a difference between the conductivity $\sigma_m$ in a prior step and the conductivity $\sigma_{m+1}$ calculated in the present step is calculated, and it is determined whether an absolute value of the difference is smaller than a preset value '$\epsilon$' or not. The equations (14) and (15) are calculated repeatedly by increasing the 'm' until the calculated difference becomes smaller than the preset value '$\epsilon$'. If the absolute value of the difference of the conductivity $\sigma_m$ in the prior step and the conductivity $\sigma_{m+1}$ in the present step is smaller than the preset value '$\epsilon$', the conductivity $\sigma_{m+1}$ is taken as the true conductivity. Then the measuring object 'S' is visualized by using the calculated conductivity $\sigma_{m+1}$.

However, even if the calculated conductivity $\sigma_{m+1}$ has taken the true magnetic flux density $B_z^j$ into account, the calculated conductivity $\sigma_{m+1}$ may have scaling difference from the true conductivity. For example, though the calculated conductivity $\sigma_{m+1}$ has a value varied with the magnetic flux density $B_z^j$, the calculated conductivity $\sigma_{m+1}$ may be greater or smaller than the true conductivity. For eliminating the scaling difference between the calculated conductivity $\sigma_{m+1}$ and the true conductivity, in the present invention, the measured surface voltage $V^j|_{\partial S}$ and the calculated surface voltage $V_{m+1}^j|_{\partial S}$ may be used for scaling the conductivity $\sigma_{m+1}$. In other words, the conductivity $\sigma_{m+1}$ is multiplied or divided by a ratio of the measured surface voltage $V^j|_{\partial S}$ to the calculated surface voltage $V_{m+1}^j|_{\partial S}$. Thus, the conductivity $\sigma_{m+1}$ is calculated correctly.

In addition, the conductivity $\sigma_{m+1}$ is substituted into the equation (15) to calculated a voltage depending on the conductivity $\sigma_{m+1}$, i.e., the voltage $V^j$ inside of the measuring object 'S' is calculated. Then, by using the conductivity $\sigma_{m+1}$ and the voltage $V^j$, the current density $J^j$ is calculated, and by using the current density $J^j$, the inside of the measuring object 'S' is visualized.

THIRD EMBODIMENT

The measuring object 'S' is placed in the MRI scanner 200, and the pairs of the current injecting devices 100 are selected one by one in succession, and the current $I^j$ (j=1, 2, - - -, N) is supplied to an inside of the measuring object 'S' through the pair of the current injecting devices 100 selected in succession. The MRI scanner 200 measures the magnetic flux densities $B^1z$, $B^2z$, ... $B^Nz$ due to the currents $I^1$, $I^2$, ..., $I^N$ injected into the measuring object 'S' respectively, the non-selected current injecting devices 100 measure a surface voltage $V^j|_{\partial S}$ of the measuring object 'S' when the selected pair of the current injecting devices 100 injects the current into the measuring object 'S'.

Figure 6A:
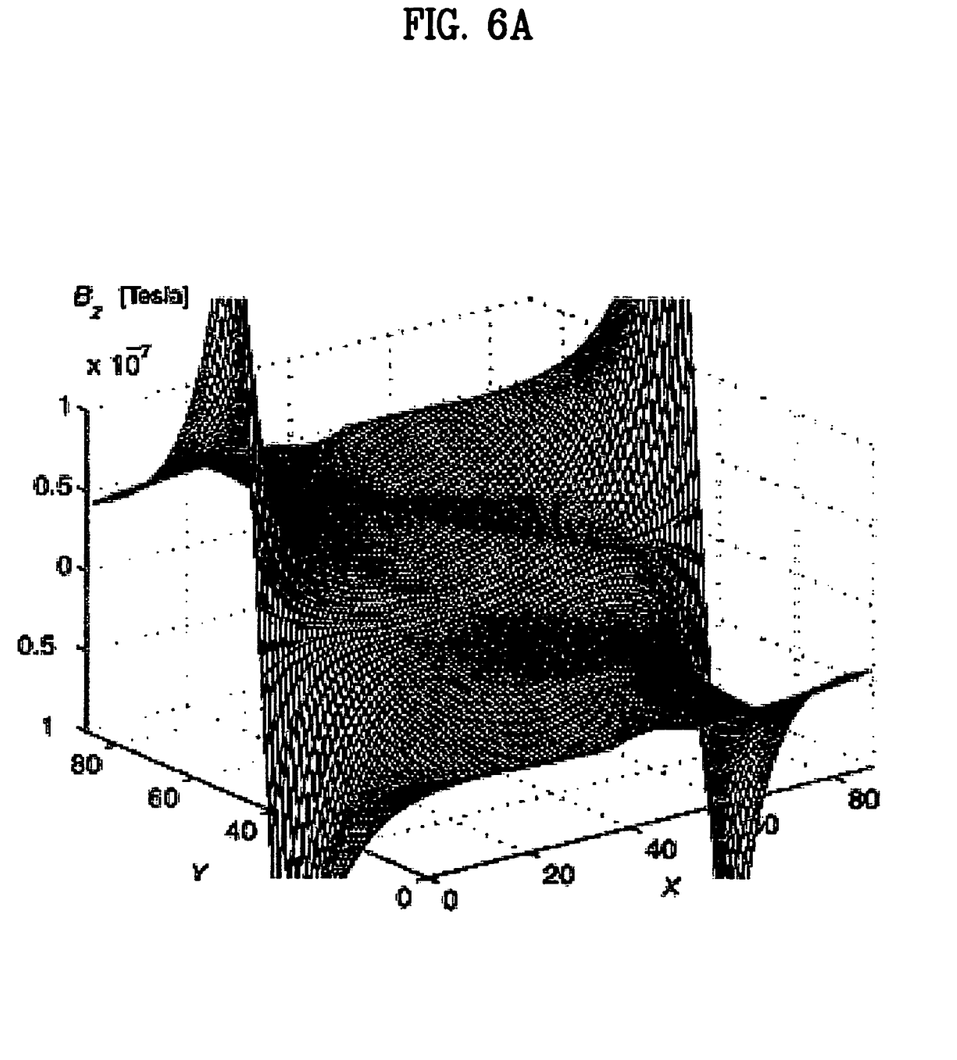
FIG. 6A illustrates an ideal image of the magnetic flux density in which noises are not included.
Figure 6B:
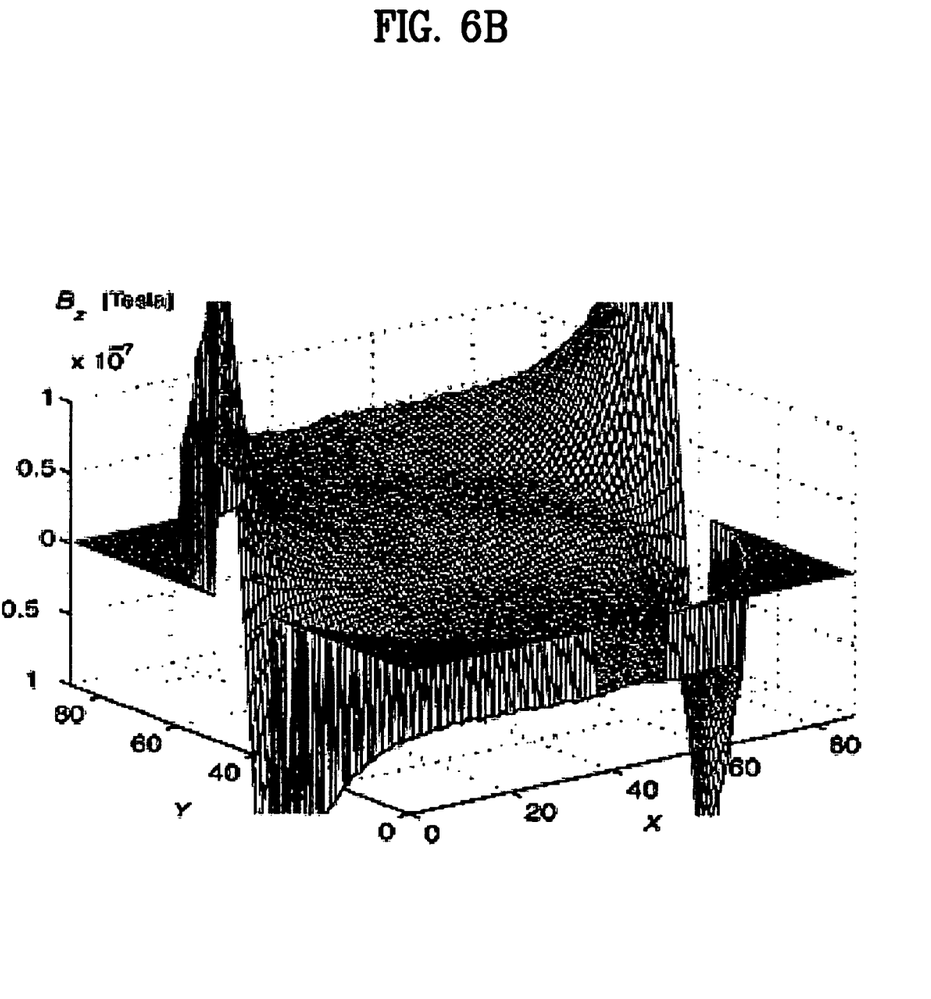
FIG. 6B illustrates an image of the magnetic flux density in which noises are included.

FIG. 6A illustrates an ideal image of the magnetic flux density not including the noises, FIG. 6B illustrates an image of the magnetic flux density including the noises. Referring to FIG. 6B, the measured magnetic flux density $B^j_z$ includes the noises due to the mechanical errors of the MRI scanner 200 and the environmental factors. In order to remove the noises from the measured magnetic flux density $B^j_z$, the operating unit 300 divides the measured magnetic flux density $B^j_z$ into the first part $B^h_z$ and the second part $B^f_z$.

The operating unit 300 calculates the first part $B^h_z$ of the measured magnetic flux density based on the following equation (16) satisfying the boundary condition in order to separate the first part $B^h_z$ and the second part $B^f_z$.

$$\nabla^2 B^h_z = 0 \quad (16)$$

The operating unit 300 calculates the difference between the measured magnetic flux density $B^j_z$ and the first part $B^h_z$ in order to obtain the second part $B^f_z$.

Figure 6C:
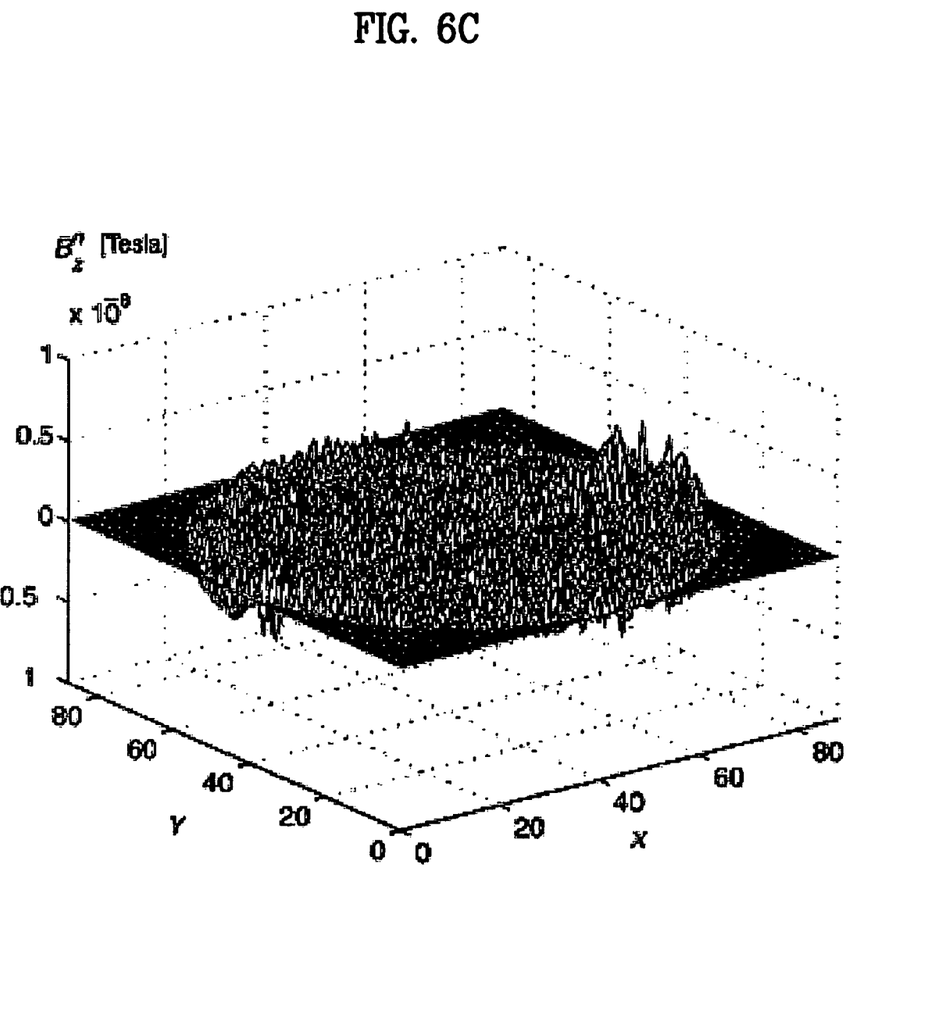
FIG. 6C illustrates a second part of the magnetic flux density in which information representing delicate patterns and edges in the measuring object is included and noises are included.
Figure 6D:
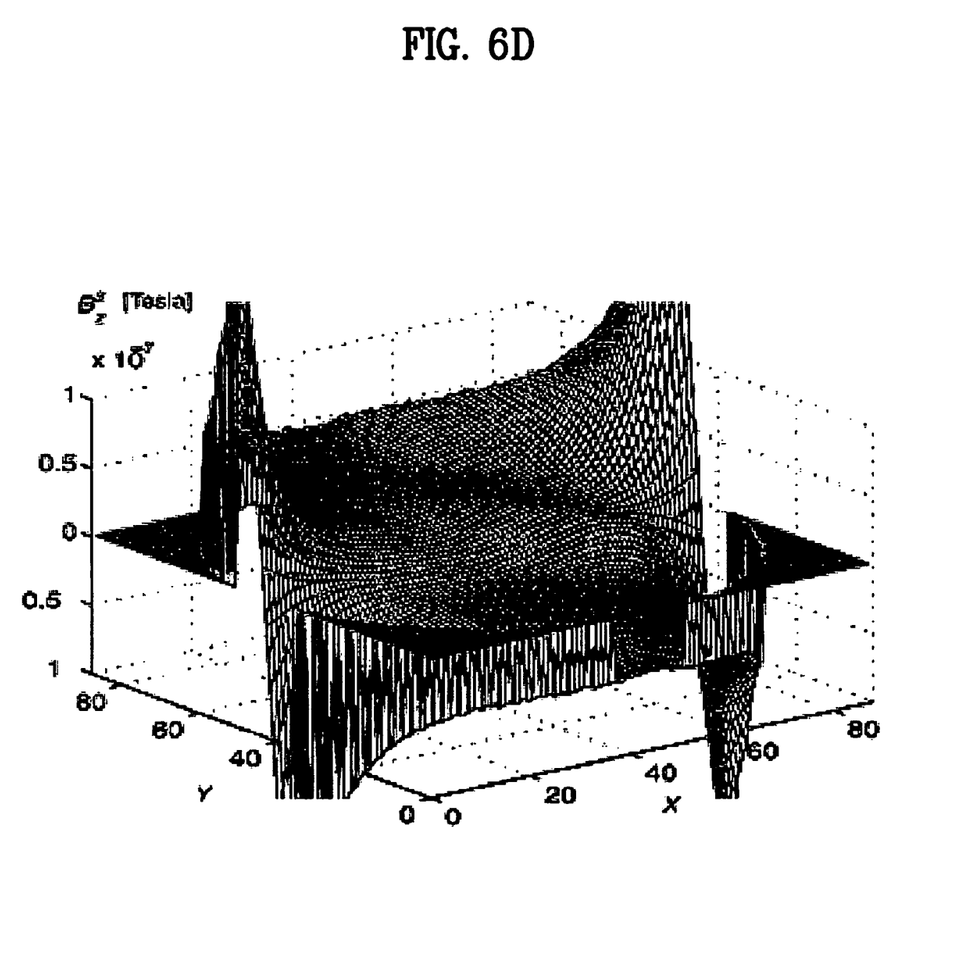
FIG. 6D illustrates a first part of the magnetic flux density in which baseline information representing sluggish patterns and edges in the measuring object is included.

FIG. 6C illustrates the second part $B^f_z$ of the magnetic flux density including information representing delicate patterns and edges in the measuring object and the noises, and FIG. 6D illustrates the first part $B^h_z$ of the magnetic flux density including baseline information representing sluggish the patterns and the edges in the measuring object.

The noises should be removed from the second part $B^f_z$ of the magnetic flux density. In the present invention, for removing the noises from the second part $B^f_z$, two diffusion coefficients are suggested. A first diffusion coefficient is based on information related to the preliminary MRI magnitude image provided by the MRI scanner 200. The information related to the preliminary MRI magnitude image depends on the intensity variation $\nabla M$ of the preliminary MRI magnitude image, and includes the information representing the patterns and the edges in the measuring object 'S'. A second diffusion coefficient is based on the space gradient $\nabla u$ of the image corresponding to the second part $B^f_z$. The following equation (17) shows the diffusion model including the first and the second diffusion coefficients $$\frac{\partial u}{\partial t} = \nabla[\Phi(|\nabla M|)\Psi(|\nabla u|)\nabla u] \quad (17)$$

Wherein, an initial condition includes $u(x,y,0)=B^f_z(x,y)$, and the function $\Psi(\nabla u)$ represents $$\frac{1}{\sqrt{|\nabla u|^2 + 1}}.$$

The operating unit 300 may remove the noises from the second part $B^f_z$ by using at least one of the two diffusion coefficients. The first diffusion coefficient is used to prevent from blurring $B^f_z$ along the boundary of the tissues in the measuring object 'S' using the intensity variation $\nabla M$ of the preliminary MRI magnitude image. The second diffusion coefficient is used to preserve edge information of the image $B^f_z$ using the space gradient $\nabla u$ of the image corresponding to the second part $B^f_z$.

After the noises are removed from the second part $B^f_z$, the operating unit 300 combines the first part $B^h_z$ and the second part $B^f_z$. Thus the denoised magnetic flux density may be obtained.

The magnetic flux density can not be measured in a portion of the measuring object 'S' filled with the air. Therefore, the operating unit 300 detects the border between the portion with the air and the portion without the air from the MR magnitude image, and calculates the magnetic flux density $B^b_z$ in the portions filled with the air on the basis of the magnetic flux density $B^j_z$ measured at the border of the portions. That is, the operating unit 300 may calculate the magnetic flux density in the portion with the air by substituting the solution of the Laplace's equation $\nabla^2 B_z = 0$ in the portion with the boundary condition having the magnetic flux density measured at the border. Then the operating unit 300 applies the denoised magnetic flux density $B^j_z$ and the calculated magnetic flux density $B^b_z$ to the algorithm suggested in the first embodiment or the second embodiment in order to calculate the conductivity $\sigma$ and the current density $J^j$.

INDUSTRIAL APPLICABILITY

As has been described, the present invention permits to obtain a conductivity distribution image and a current density distribution image of an inside of a measuring object without rotating the measuring object, such as a human body, or a substance, within an MRI scanner.

Moreover, the present invention permits to produce a high quality image by removing the noises from the measured magnetic flux density successfully and calculating the magnetic flux density in the tissue filled with the air or water on the basis of the magnetic flux density measured at the border of the tissue.

Furthermore, the conductivity distribution image and the current density distribution image can be applicable to the present medical equipment. According to this, a functional imaging can be provided for organs each of which biological tissue conductivity varies with physiologic action, to secure a new medical examination technology. For an example, an image required for measuring a volume of a lung varies with respiration (a measurement by using variation of a resistivity of the lung in inhale and exhale of air), a measurement of an cardiac output of a heart, a measurement of a stomach, a measurement of cystic residual urine, a measurement of a healed state of a bone fracture, or a measurement of a brain function.

Since quantitative electric properties of a human tissue can be known, optimization of diagnosis equipments, and treatment equipments using electro-magnetic energy, such as various electric/magnetic stimulators, defibrillators, cardiac pacemakers, and the like, is made possible.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A system for visualizing conductivity and current density distributions comprising:

a plurality of current injecting devices for injecting currents into a measuring object;

a measuring unit for measuring a magnetic flux density due to the currents injected into a measuring object;

an operating unit for selecting one pair of the current injecting devices in succession so as to inject currents of different directions into the measuring object, and calculating directional components of an anisotropic conductivity inside of the measuring object on the basis of the measured magnetic flux density; and displaying means for visualizing an inside of the measuring object by using the calculated directional components of the anisotropic conductivity.

2. The system as claimed in claim 1, wherein the selected pair of the current injecting devices apply the current to the measuring object, and one or more non-selected pairs of the current injecting devices measure a surface voltage of the measuring object.

3. The system as claimed in claim 1, wherein the operating unit calculates an inside voltage and a surface voltage of the measuring object on the basis of an arbitrary conductivity, and calculates the directional components of the anisotropic conductivity on the basis of the calculated inside voltage and the measured magnetic flux density.

4. The system as claimed in claim 3, wherein the operating unit multiplies or divides the calculated directional components of the anisotropic conductivity by a ratio of the calculated surface voltage to a surface voltage measured by the current injecting devices.

5. The system as claimed in claim 3, wherein, if an absolute value of a difference between the arbitrary conductivity and the calculated anisotropic conductivity is greater than a preset value, the operating unit calculates new directional components of the anisotropic conductivity on the basis of a calculated inside voltage depending on the calculated directional components.

6. The system as claimed in claim 3, wherein the operating unit determines that the calculated anisotropic conductivity is a true conductivity, if an absolute value of the difference between the arbitrary conductivity and the calculated anisotropic conductivity is smaller than a present value.

7. The system as claimed in claim 3, wherein the operating unit calculates the current density distributions inside of the measuring object on the basis of the calculated inside voltage and the measured magnetic flux density, and calculates a z-directional component on the basis of the calculated inside voltage and the calculated current density distributions.

8. The system as claimed in claim 1, wherein the operating unit divides the measured magnetic flux density into a first part not including noises and a second part including the noises, removes the noises from the second part, and combines the first part and the second part.

9. The system as claimed in claim 1, wherein the measuring unit measures the magnetic flux density corresponding to one direction parallel to a main magnetic field thereof.

10. A method for visualizing conductivity and current density distributions, comprising:

(a) injecting currents of different directions into a measuring object through current injecting devices attached to a surface of the measuring object;

(b) measuring a magnetic flux density due to the injected currents;

(c) calculating directional components of an anisotropic conductivity inside of the measuring object on the basis of the measured magnetic flux density; and (d) visualizing an inside of the measuring object by using the calculated directional components of the anisotropic conductivity.

11. The method as claimed in claim 10, wherein the injecting currents of different directions into the measuring object comprises:

selecting a pair of the current injecting devices in succession, and injecting the currents into the measuring object in succession through the selected pair of the current injecting devices.

12. The method as claimed in claim 11, further comprises measuring a surface voltage of the measuring object through non-selected current injecting devices.

13. The method as claimed in claim 10, wherein the measuring the magnetic flux density comprises measuring the magnetic flux density corresponding to one direction parallel to a main magnetic field.

14. The method as claimed in claim 10, wherein the calculating the directional components of the anisotropic conductivity comprises:

calculating an inside voltage and a surface voltage of the measuring object on the basis of an arbitrary conductivity, and calculating the directional components of the anisotropic conductivity on the basis of the calculated inside voltage and the measured magnetic flux density.

15. The method as claimed in claim 14, further comprises multiplying or dividing the calculated directional components of the anisotropic conductivity by a ratio of the calculated surface voltage and a measured surface voltage of the measuring object.

16. The method as claimed in claim 14, further comprises calculating an absolute value of a difference of the arbitrary conductivity and the calculated anisotropic conductivity, and comparing the absolute value of the difference to a preset value.

17. The method as claimed in claim 16, further comprises calculating new directional components of the anisotropic conductivity on the basis of a calculated inside voltage depending on the calculated directional components if the absolute value of the difference of the arbitrary conductivity and the measured anisotropic conductivity is greater than the preset value.

18. The method as claimed in claim 16, further comprises determining that the calculated anisotropic conductivity is a true conductivity, if the absolute value of the difference of the arbitrary conductivity and the calculated anisotropic conductivity is smaller than the present value.

19. The method as claimed in claim 14, the calculating directional components of the anisotropic conductivity comprises:

calculating five directional components of the anisotropic conductivity on the basis of the calculated inside voltage and the measured magnetic flux density;

calculating the current density distributions inside of the measuring object on the basis of the calculated inside voltage and the measured magnetic flux density; and calculating one directional component of the anisotropic conductivity on the basis of the calculated inside voltage and the calculated current density distributions.

20. The method as claimed in claim 10, further comprising:
dividing the measured magnetic flux density into a first part not including noises and a second part including the noises;
removing the noises from the second part; and
combining the first part and the second part.

21. The method as claimed in claim 20, wherein the dividing the measured magnetic flux density into the first and second parts comprises:
calculating the first part not including the noises by substituting the measured magnetic flux density to a preset algorithm; and
calculating a difference of the measured magnetic flux density and the calculated first part.

22. The method as claimed in claim 20, wherein the removing the noises from the second part comprises removing the noises from the second part on the basis of an intensity variation of an MRI magnitude image.

23. The method as claimed in claim 10, wherein the removing the noises from the second part comprises removing the noises from the second part on the basis of a spatial gradient of an image corresponding to the second part.

24. The method as claimed in claim 10, further comprises calculating a magnetic flux density of a portion in which the magnetic flux density is not measured, on the basis of the magnetic flux density measured at a border of the portion.

25. A system for visualizing conductivity and current density distributions comprising:
a plurality of current injecting devices for injecting currents into a measuring object;
a measuring unit for measuring a magnetic flux density due to the currents injected into a measuring object; and
an operating unit for dividing the measured magnetic flux density into a first part not including noises and a second part including the noises, and combining the first part and the second part after removing the noises from the second part.

26. The system as claimed in claim 25, wherein the operating unit removes the noises from the second part on the basis of an intensity variation of an MRI magnitude image.

27. The system as claimed in claim 25, wherein the operating unit removes the noises from the second part on the basis of a spatial gradient of an image corresponding to the second part.

28. The system as claimed in claim 25, wherein the operating unit calculates a magnetic flux density of a portion in which the magnetic flux density is not measured, on the basis of the magnetic flux density measured at a border of the portion.

29. A method for visualizing conductivity and current density distributions, comprising:
(a) injecting currents into a measuring object through current injecting devices attached to a surface of the measuring object;
(b) measuring a magnetic flux density of due to the injected currents;
(c) dividing the measured magnetic flux density into a first part not including noises and a second part including the noises;
(d) removing the noises from the second part; and (e) combining the first part and the second part.

30. The method as claimed in claim 29, wherein the dividing the measured magnetic flux density into the first part and the second part comprises: calculating the first part by applying the measured magnetic flux density to a preset algorithm; and calculating a difference between the measured magnetic flux density and the calculated first part.

31. The method as claimed in claim 29, wherein the removing the noises from the second part comprises removing the noises from the second part on the basis of an intensity variation of an MRI magnitude image.

32. The method as claimed in claim 29, wherein the removing the noises from the second part comprises removing the noises from the second part on the basis of a spatial gradient of an image corresponding to the second part.

33. The method as claimed in claim 29, further comprises calculating a magnetic flux density of a portion in which the magnetic flux density is not measured, on the basis of the magnetic flux density measured at a border of the portion.

* * * * *